US 9,157,876 B2

(12) United States Patent
Halderman et al.

(10) Patent No.: US 9,157,876 B2
(45) Date of Patent: Oct. 13, 2015

(54) METHOD AND APPARATUS FOR CHARACTERIZING OBJECTS AND MONITORING MANUFACTURING PROCESSES

(75) Inventors: Jonathan D. Halderman, Santa Clara, CA (US); Ciaran John Patrick O'Connor, Bozeman, MT (US); Jay Wilkins, Belgrade, MT (US)

(73) Assignee: ELECTRO SCIENTIFIC INDUSTRIES, INC., Portland, OR (US)

( * ) Notice: Subject to any disclaimer, the term of this patent is extended or adjusted under 35 U.S.C. 154(b) by 613 days.

(21) Appl. No.: 13/557,545

(22) Filed: Jul. 25, 2012

(65) Prior Publication Data

US 2013/0030717 A1 Jan. 31, 2013

Related U.S. Application Data

(60) Provisional application No. 61/511,197, filed on Jul. 25, 2011.

(51) Int. Cl.
*G06F 19/00* (2011.01)
*G01N 23/225* (2006.01)
*H01L 21/66* (2006.01)
*H01L 33/00* (2010.01)

(52) U.S. Cl.
CPC .............. *G01N 23/225* (2013.01); *H01L 22/12* (2013.01); *H01L 33/0095* (2013.01)

(58) Field of Classification Search
CPC ............................. C12Q 1/686; C12Q 1/6874
USPC ......................................... 702/160, 182–185
See application file for complete search history.

(56) References Cited

U.S. PATENT DOCUMENTS

| | | |
|---|---|---|
| 5,521,525 A | 5/1996 | Nicollian et al. |
| 5,719,796 A | 2/1998 | Chen |
| 6,037,588 A | 3/2000 | Liu et al. |
| 6,274,449 B1 | 8/2001 | Vasanth et al. |
| 6,311,096 B1 | 10/2001 | Saxena et al. |
| 6,326,220 B1 | 12/2001 | Chen et al. |
| 6,542,830 B1 | 4/2003 | Mizuno et al. |
| 6,622,059 B1 | 9/2003 | Toprac et al. |
| 6,638,778 B1 | 10/2003 | Peterson et al. |

(Continued)

OTHER PUBLICATIONS

EAG Evans Analytical Group, "Analytical Technique Chart", 2 pages.

(Continued)

*Primary Examiner* — Edward Raymond
(74) *Attorney, Agent, or Firm* — Haynes Beffel & Wolfeld LLP

(57) ABSTRACT

A method of characterizing an object includes determining a depth-wise composition of the object at a measurement site within the object. A property of the object within a region adjacent to the measurement site can, optionally, be estimated based on the determining. Another method of characterizing an object includes disposing at least a portion of an object within a measurement region of a metrology tool, aligning a feature of the object and a location of a designated measurement site within the measurement region relative to each other, and performing a performing a compositional analysis of a portion of the object occupying the measurement site. Various apparatus for performing these methods are also disclosed, as are methods of monitoring manufacturing processes based on these methods.

24 Claims, 5 Drawing Sheets

(56) References Cited

U.S. PATENT DOCUMENTS

| | | | |
|---|---|---|---|
| 6,694,284 B1 * | 2/2004 | Nikoonahad et al. | 702/155 |
| 6,757,621 B2 | 6/2004 | Mizuno et al. | |
| 7,074,270 B2 | 7/2006 | Sato et al. | |
| 7,298,496 B2 | 11/2007 | Hill | |
| 7,379,924 B1 | 5/2008 | Marathe et al. | |
| 7,403,023 B2 | 7/2008 | Steeples et al. | |
| 7,411,188 B2 | 8/2008 | deCecco et al. | |
| 7,462,502 B2 | 12/2008 | Paolini et al. | |
| 7,512,499 B1 | 3/2009 | Bu et al. | |
| 7,884,321 B2 | 2/2011 | deCecco et al. | |
| 7,974,801 B2 | 7/2011 | Good | |
| 2002/0018217 A1 | 2/2002 | Weber-Grabau et al. | |
| 2003/0111447 A1 | 6/2003 | Corkum et al. | |
| 2008/0036464 A1 | 2/2008 | Steeples et al. | |
| 2009/0072263 A1 | 3/2009 | Paolini et al. | |
| 2009/0261358 A1 | 10/2009 | Chitnis et al. | |
| 2009/0276075 A1 | 11/2009 | Good et al. | |
| 2010/0051805 A1 | 3/2010 | Rahman et al. | |
| 2010/0138026 A1 | 6/2010 | Kaushal et al. | |
| 2010/0271621 A1 | 10/2010 | Levy et al. | |
| 2010/0332208 A1 | 12/2010 | Victory et al. | |
| 2011/0129947 A1 | 6/2011 | Mangum et al. | |
| 2011/0237005 A1 | 9/2011 | Kim et al. | |
| 2011/0246169 A1 | 10/2011 | Sakamoto | |
| 2011/0313748 A1 | 12/2011 | Li | |

OTHER PUBLICATIONS

International Search Report of PCT/US2012/048090, 2 pages.
Written Opinion of PCT/US2012/048090, 2 pages.

* cited by examiner

METHOD AND APPARATUS FOR CHARACTERIZING OBJECTS AND MONITORING MANUFACTURING PROCESSES

CROSS REFERENCE TO RELATED APPLICATIONS

This application claims the benefit of U.S. Provisional Application No. 61/511,197, filed Jul. 25, 2011, the contents of which are incorporated herein by reference.

BACKGROUND

Embodiments of the present invention are directed to methods and systems for characterizing an object. Embodiments of the present invention are also directed to methods and systems for monitoring manufacturing processes and production yield associated with an object based on a compositional analysis of the object.

Global market trends are inducing manufacturers to produce products while improving process tool utilization and decreasing performance variability in the final products produced. This holds especially true in the manufacture of products such as active solid-state electronic devices (e.g., diodes, transistors, thyristors, and other devices that operate by movement of charge carriers), electronic displays (e.g., liquid crystal display, light emitting diode displays, organic light emitting diode displays, etc.), photonics devices, biomedical devices, pharmaceutical products, and the like. Process sequences used to manufacture these products can be complex, and a subtle change in one aspect of the manufacturing process may have a deleterious impact on the ability to manufacture products with desirably consistent performance properties.

SUMMARY

One embodiment of the present described herein can be exemplarily characterized as a method that includes determining, at a measurement site within an object, a composition of the object as a function of depth within the object; and based on the determining, quantitatively estimating at least one property of the object within a region of the object adjacent to the measurement site.

Another embodiment of the present described herein can be exemplarily characterized as a method of monitoring a manufacturing process implementable by manufacturing system including at least one process apparatus, wherein the method includes determining, at a measurement site within an object, a composition of the object as a function of depth within the object; based on the determining, quantitatively estimating at least one property of the object within a region of the object adjacent to the measurement site; generating regional property data based on the quantitative estimating; and providing the estimated property data to a controller coupled to a process apparatus of the manufacturing system configured to manufacture the object or modify the object.

Yet another embodiment of the present described herein can be exemplarily characterized as a method that includes providing a metrology tool that includes a measurement region within which an object is at least partially disposable; a controller configured to designate a zone within the measurement region as a measurement site; and a measurement system coupled to the controller, wherein the measurement system is configured to perform a compositional analysis of material occupying the measurement site. The method may further include disposing at least a portion of an object within the measurement region, wherein the object includes a feature; aligning the feature and a location of the measurement site within the measurement region relative to each other; and performing a compositional analysis of the portion of the disposed object occupying the measurement site.

Further embodiments, forms, objects, features, advantages, aspects, and benefits shall become apparent from the following description and drawings.

DETAILED DESCRIPTION OF THE ILLUSTRATED EMBODIMENTS

Figure 1:
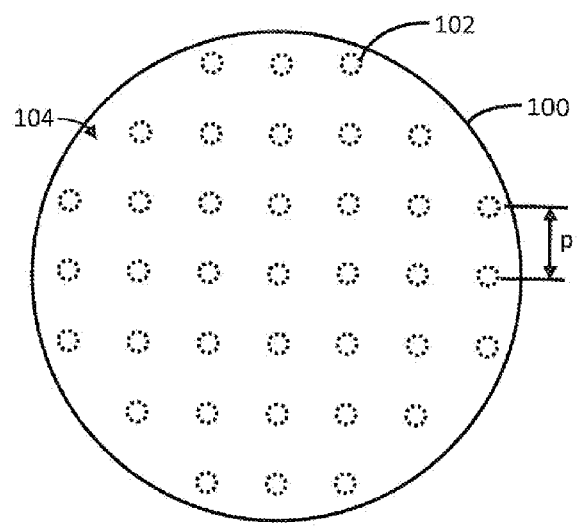
FIG. 1 is a schematic view illustrating an exemplary arrangement of measurement sites distributed across an object according to one embodiment of the present invention.

Exemplary embodiments of the present invention will be described more fully hereinafter with reference to the accompanying drawings. It will be appreciated that these embodiments may be altered and implemented in many other forms and should not be construed as limited to the discussion set forth herein. Rather, these embodiments are provided so that this disclosure will be thorough and complete, and will fully convey the scope of the invention to those skilled in the art. In the drawings, the sizes and relative sizes of layers and regions may be exaggerated for clarity.

The terminology used herein is for the purpose of describing particular example embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments disclosed herein are directed to methods and apparatus for characterizing objects and monitoring manufacturing processes (e.g., used to fabricate or modify such objects). Examples of objects that can be characterized according to embodiments described herein include substrates such as those used in the manufacture of integrated circuits (ICs), power ICs, radio frequency (RF) devices, photovoltaic cells, thermoelectric devices, liquid crystal display (LCD) panels, light-emitting diodes (LEDs), LED displays, organic LEDs (OLEDs), OLED displays, etc. (e.g., silicon substrates, silicon dioxide substrates, aluminum oxide substrates, sapphire substrates, germanium substrates, gallium arsenide substrates, silicon-germanium substrates, indium phosphide substrates, aluminum nitride substrates, silicon carbide substrates, glass sheets, polymer sheets, etc.). Any of these substrates may be provided as an unprocessed substrate or as a substrate that has been subjected to at least one manufacturing process (e.g., doping, ion implantation, etching, deposition, patterning, dicing, etc.). Consequently, a substrate may be provided as a wafer (intrinsic or doped) that is either bare or that has at least one structure or feature (e.g., doped region, dielectric layer, transistor, capacitor, resistor, conductive structure, semiconductive structure, light-absorbing layer, epitaxial layer, anti-reflective coating, etc.) formed within the wafer or on or over the wafer surface. It will be appreciated that embodiments exemplarily described herein can be applied to characterize objects that do not include substrates such as those as described above. Such objects may, for example, include archaeological materials, biological assay substrates and other biological materials, ceramics, geological materials, pharmaceutical agents (e.g., pills), metals, polymers, petrochemical materials, etc.

Generally, an object can be characterized by determining, at a plurality of discrete measurement sites within the object, a depth-wise composition of the object. For example, with reference to FIG. 1, the depth-wise composition of an object such as object 100 (e.g., a sapphire substrate having a plurality of layers formed thereon) can be determined at a plurality of discrete measurement sites, such as measurement sites 102, distributed across the object 100 in an arrangement 104. A minimum center-to-center distance, or pitch (p), between pairs reference cites 102 can be in a range from 0.1 mm to 10 mm. It will be appreciated that the pitch, p, may be less than 0.1 mm or greater than 10 mm depending on, for example, the maximum dimension of the object 100, the desired resolution of the characterization, the actual or anticipated variation of composition throughout the object 100, or the like or a combination thereof. The maximum dimension of the object (e.g., the diameter of object 100, as illustrated) can be in a range from 50 mm to 450 mm (e.g., 50 mm, 150 mm, 300 mm, 400 mm, 450 mm, or the like). It will be appreciated that the maximum dimension of the object can be less than 50 mm (e.g., less than or equal to 25 mm, less than or equal to 10 mm, or the like) or greater than 450 mm (e.g., greater than or equal to 500 mm, greater than or equal to 700 mm, greater than or equal to 900 mm, greater than or equal to 1 m, or the like). It will be appreciated that the arrangement 104 may contain any number of measurement sites 102 (e.g., one measurement site 102, two measurement sites 102, three measurement sites 102, fifty measurement sites 102, or the like) depending on, for example, the maximum dimension of the object 100, the desired resolution of the characterization, the actual or anticipated variation of composition throughout the object 100, or the like or a combination thereof.

As exemplarily illustrated, the arrangement 104 may be provided such that the distribution of measurement sites 102 across the object 100 is at least substantially uniform. In other embodiments, however, the arrangement 104 may be provided such that measurement sites 102 are randomly distributed across the object 100. In still other embodiments, the measurement sites 102 may be distributed across the object 100 in multiple arrangements such that a pitch between pairs of measurement sites 102 in one arrangement is different from a pitch between pairs of measurement sites 102 in another arrangement, such that measurement sites 102 in one arrangement are generally oriented differently with respect to the object 100 than measurement sites 102 in another arrangement, or the like or a combination thereof.

The depth-wise composition of the object at an arbitrary measurement site 102 of the object 100 can be described as the composition of the object (also referred to herein as the "object composition") as a function of depth within the object 100. For example, with reference to the chart 200 shown in FIG. 2, the object composition can be represented in terms of a measured amount of an element (e.g., measured in parts-per-million, parts-per-billion, etc.) within the object 100 as a function of depth within the object 100 (e.g., measured in micrometers, nanometers, etc., from a surface of the object 100). In the illustrated example, lines 202, 204, 206, 208 and 210 represent the measured amounts of gallium, magnesium, indium, silicon and aluminum, respectively, within over a range of depths within the object 100. In the illustrated example, the depth-wise composition described by chart 200 indicates that the object 100 includes a multiple quantum well (MQW) LED structure having a p-GaN region 212 and an MQW region 214. It will be appreciated, however, that the object 100 can have any depth-wise elemental composition depending upon the particular function intended for the object 100. In other embodiments, the object composition can be described in terms of a measured concentration, or the like, of an element, isotope, compound, etc., as a function of depth with the object 100.

It will be appreciated that the depth-wise object composition can be determined for one or more or all of the measurement sites 102 by any suitable or desirable method. For example, the depth-wise object composition can be determined using a non-destructive technique, a destructive technique or a combination thereof. Examples of non-destructive techniques that may be used to determine depth-wise object composition include photoluminescence, spectroscopic ellipsometry, confocal microscopy, or the like or a combination thereof. Examples of destructive techniques that may be used to determine depth-wise object composition include glow discharge optical emission spectroscopy (GDOES), glow discharge mass spectroscopy (GDMS), laser ablation inductively coupled plasma mass spectroscopy (LAICPMS), laser ablation inductively coupled optical emission spectroscopy (LAICPOES), laser induced breakdown spectroscopy (LIBS), secondary ion mass spectroscopy (SIMS), focused ion beam optical emission spectroscopy (FIBOES), or the like or a combination thereof.

Figure 3:
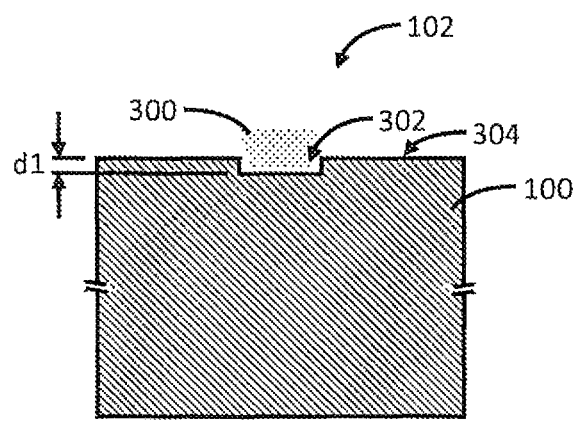
FIGS. 3 and 4 illustrate an exemplary method of obtaining a sample of an object to determine a depth-wise object composition.

Generally, destructive techniques used to determine a depth-wise object composition can include obtaining a sample of the object 100 (e.g., by removing a portion of the object 100) and analyzing the composition of the obtained sample. For example, and with reference to FIG. 3, a portion of the object 100 may be removed to form a sample 300 (e.g., a plume containing materials removed from the object 100). As shown in FIG. 3, material in the sample 300 is removed from a portion of the object 100 to form pit or crater 302 extending a depth "dl" below the surface 304 of the object 100 at a measurement site 102. Thus, the composition of the sample 300 corresponds to the material composition removed from the portion of object 100 used to form the pit 302. The sample 300 may be transported to any suitable sample analysis apparatus capable of performing compositional analysis on the sample 300 by mass spectroscopy, optical emission spectroscopy, atomic absorption spectroscopy, atomic fluorescence spectroscopy, or the like or a combination thereof. In one embodiment, the sample 300 is transported via a transport conduit having one end proximate to the surface 304 of the object 100 at the measurement site 102 and a second end proximate to the sample analysis apparatus.

Figure 4:
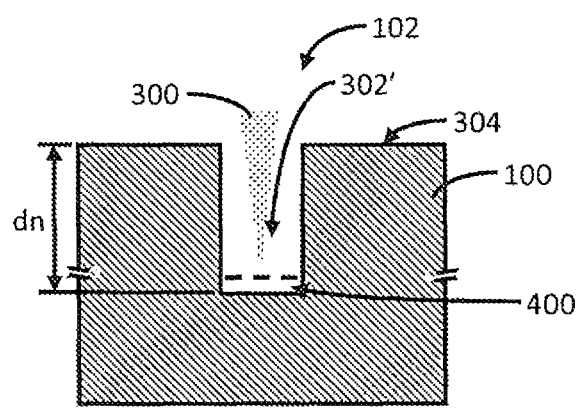

The removal process described above with respect to FIG. 3 may be performed to increase the depth of the pit 302. As shown in FIG. 4, the removal process can be performed to form an extended pit or crater 302' that extends a desired depth "dn" below the surface 304 of the object at the measurement site 102. Thus, the composition of the sample 300 shown in FIG. 4 corresponds to the material composition removed from the portion of object 100 used to form the lower portion (e.g., portion 400) of the extended pit 302'.

In one embodiment, the removal process is performed continuously such that the sample 300 is continuously produced (e.g., from the time when the pit 302 is initially formed until the time when the extended pit 302' extends the desired depth "dn" below the surface 304 of the object 100 at the measurement site 102). In such an embodiment, the sample analysis apparatus can be configured to continuously analyze the sample 300 produced during formation of the extended pit 302', can be configured to periodically analyze the sample 300 produced during formation of the extended pit 302'.

In another embodiment, the removal process is repeatedly performed such that a series of samples 300 are discretely and sequentially produced (e.g., from the time when the pit 302 is initially formed until the time when the extended pit 302' extends the desired depth "dn" below the surface 304 of the object 100 at the measurement site 102). In such an embodiment, the sample analysis apparatus can be configured to continuously individually analyze one or more or all of the sample 300 discretely produced during formation of the extended pit 302'.

The depth "dn" of the extended pit 302' can be calculated, estimated or otherwise determined by any suitable method. For example, the depth "dn" can be determined by correlating the anticipated, estimated or actual time required to form the extended pit 302' with predetermined, estimated or otherwise predicted material removal rates associated with the removal process used to form the extended pit 302'. In another example (e.g., when a series of discrete samples 300 are produced), the depth "dn" can be determined by correlating the anticipated, estimated or actual number of samples 300 produced to form the extended pit 302' with predetermined, estimated or otherwise predicted material removal rates associated with the removal process used to produce each discrete sample 300.

The sample 300 may be objected by any suitable method. For example, the sample 300 may be obtained by evaporating, sublimating, ionizing, ablating, etc., a portion of the object 100. In one embodiment, a sample 300 may be produced by directing a beam of laser pulses onto the object 100. Parameters of the beam of laser pulses can be selected to ablate a portion of the object 100, such that the sample 300 is generated upon directing one or more laser pulses onto the object 100. The beam of laser pulses may have a laser fluence in a range from 0.1 J/cm$^2$ to 30 J/cm$^2$, a laser pulse duration of 150 fs to 20 ns, a wavelength in a range from 193 nm to 266 nm, and a pulse repetition rate in a range from 1 Hz to 100 Hz. In one embodiment, the beam of laser pulses may have a laser fluence of 8 J/cm$^2$, a laser pulse duration of less than 5 ns, a wavelength of 193 nm, and a pulse repetition rate in a range from 1 Hz to 5 Hz. It will be appreciated, however, that parameters of the beam can be selected to be less than or greater than any of the ranges disclosed above. It will also be appreciated that parameters of the beam of laser pulses can be controlled to precisely control the depth of a pit and, thus, the amount of material contained in a sample 300. For example, parameters of an individual laser pulse can be selected to form (or incrementally extend) a pit to a depth in a range of about 10 nm to about 30 nm (e.g., 20 nm, or about 20 nm).

The method of characterizing the object 100 may optionally include quantitatively estimating at least one property (also referred to herein as a "regional property") of the object 100 within a region of the object 100. The region of the object 100 for which the regional property is quantitatively estimated may be adjacent to one or more or all of the measurement sites 102. A regional property can, for example, include a particular composition (e.g., elemental composition, isotopic composition, molecular composition, or the like or a combination thereof), an electrical property (e.g., electrical conductivity, electrical resistivity, threshold voltage, breakdown current, or the like or a combination thereof), an optical property (e.g., optical transmittance, optical reflectance, optical absorbance, optical emittance, or the like or a combination thereof), a thermal property (e.g., thermal conductivity, thermal expansion, specific heat, or the like or a combination thereof), a mechanical property (e.g., mass, thickness of the portion having a property of a particular nature, or the like or a combination thereof), a magnetic property (e.g., magnetic permeability, etc.), or the like or a combination thereof.

A regional property of the object 100 may be quantitatively estimated by any suitable method. For example, a regional property of the object 100 may be quantitatively estimated by applying a model (e.g., a parameterized model associated with the particular regional property) to the previously determined depth-wise object compositions. The model may be based on empirically determined correlations, or may be based on any other relationship between a determined depth-wise object composition and one or more regional properties associated therewith. For example, and continuing with the example embodiment discussed above with respect to FIG. 2, some exemplary regional properties can include the forward voltage (Vf) of the LED structure, centroid wavelength (Wd) of light capable of being emitted by the LED structure and the light output (Iv) of the LED structure. The forward voltage (Vf) may be quantitatively estimated upon multiplying the thickness of the P—GaN region (indicated by region 212 in FIG. 2) by the depth-wise change in magnesium content in the P—GaN region (indicated by line segment 204a in FIG. 2) and the total magnesium content in the P—GaN region (indicated by the area under line 204 at region 212 in FIG. 2). The centroid wavelength (Wd) may be quantitatively estimated upon multiplying the indium-to-aluminum ratio in the MQW region 214 in FIG. 2 by the depth-wise change in indium content in the P—GaN region (indicated by line segment 206a in FIG. 2) and the thickness of the MQW region 214 indicated in FIG. 2. The light output (Iv) may be quantitatively estimated upon multiplying the indium-to-aluminum ratio in the MQW region 214 in FIG. 2 by the depth-wise change in magnesium content in the P—GaN region (indicated by line segment 204a in FIG. 2) and the thickness of the MOW region 214 indicated in FIG. 2.

Upon applying the model for the regional property, a quantitative estimate of the regional property at one or more or all of the measurement sites 102 can be quantitatively estimated. Thereafter, techniques such as curve fitting (e.g., by least squares fits, smooth spline fits, etc.) and other statistical techniques may be applied to one or more or all of the quantitatively estimated site properties to generate a quantitative estimate the property for a region of the object 100 between one or more or all of the measurement sites 102.

It will be appreciated that the aforementioned methods and apparatus may be applied to characterize any suitable object 100, and may be implemented in a manual or automated manner. Further, in one embodiment, an apparatus capable of implementing the methods exemplarily disclosed above may be incorporated within a manufacturing system as a metrology tool useful for in-line monitoring of a manufacturing process. For example, a manufacturing system such as manufacturing system 500 may include a first process apparatus 502 and a second process apparatus 504, each configured to perform one or more manufacturing processes. Although the manufacturing system 500 is illustrated as including only two process apparatus, it will be appreciated that the manufacturing system 500 may include only a single process apparatus, or more than two process apparatus. Any process apparatus within the manufacturing system 500 can be configured to perform any desired manufacturing process. For example, a process apparatus can be provided as a deposition apparatus (e.g., sputter deposition apparatus, chemical vapor deposition (CVD) apparatus, plasma-enhanced chemical vapor deposition (PECVD) apparatus, metal-organic chemical vapor deposition (MOCVD) apparatus, atomic layer deposition (ALD) apparatus, etc.), an etching apparatus (e.g., wet etch apparatus, dry etch apparatus, etc.), a CMP apparatus, an ion implantation apparatus, or the like or a combination thereof.

Continuing with the example embodiment discussed above with respect to FIG. 2, the first process apparatus 502 may include an MOCVD apparatus configured to form at least a part of the aforementioned MQW LED structure and the second process apparatus 504 may include a dry etch apparatus configured to pattern the MQW LED structure to form contact regions for electrodes). It will be appreciated that the manufacturing system 500 may further include other process apparatus such as a singulation apparatus configured to separate LED devices ultimately formed from the MQW LED structure of the object 100 into a plurality of individual LED devices.

The manufacturing system 500 may further include a process controller 506 coupled to one or more process apparatus (e.g., to the first process apparatus 502 and the second process apparatus 504) and may be configured to control an operation of a process apparatus coupled thereto. Generally, the process controller 506 can include operating logic (not shown) that defines various control, management and/or regulation functions, and may be in the form of dedicated hardware, such as a hardwired state machine, a processor executing programming instructions, and/or a different form as would occur to those skilled in the art. Operating logic may include digital circuitry, analog circuitry, or a hybrid combination of both of these types. In one embodiment, the operating logic includes a programmable microcontroller or microprocessor, that can include one or more processing units arranged to execute software and/or firmware stored in memory (not shown). Memory can include one or more types including semiconductor, magnetic, and/or optical varieties, and/or may be of a volatile and/or nonvolatile variety. In one embodiment, memory stores programming instructions of operating logic. Alternatively or additionally, memory may store data that is manipulated by operating logic. In one arrangement, operating logic and memory are included in a controller/processor form of operating logic that manages and controls operational aspects of the first process apparatus 502 and the second process apparatus 504, although in other arrangements they may be separate.

The manufacturing system 500 may further include an object transfer system 508 configured to transfer the object 100 (e.g., under the control of the process controller 506) to and from the various process apparatus of the manufacturing system 500. The object transfer system 508 may, for example, include one or more robot transfer arms (e.g., each having a vacuum or electrostatic end-effector adapted to handle the object 100), one or more conveyor belts (e.g., configured to convey the object 100 to or from a process apparatus), or the like or a combination thereof. In one embodiment, the object transfer system 508 can include a cassette or other storage mechanism to facilitate efficient transfer of multiple objects within the manufacturing system 500.

The manufacturing system 500 may further include a metrology tool 510 configured to characterize the object 100 in the manner as exemplarily described above. Although the manufacturing system 500 is illustrated as including only one metrology tool 510, it will be appreciated that the manufacturing system 500 may include any number of metrology tools 510 configured to characterize objects fabricated by any process apparatus included within the manufacturing system 500.

As exemplarily illustrated, the metrology tool 510 can include a measurement region 512, a measurement system 514 and a metrology controller 516. Generally, the measurement region 512 is configured to receive at least a portion of the object 100. In one embodiment, the object transfer system 508 can be configured to transfer the object 100 into the measurement region 512 (e.g., from the first process apparatus 502) and/or out of the measurement region 512 (e.g., to the second process apparatus 504). The measurement system 514 is configured to determine the depth-wise composition of the object 100 (e.g., at one or more measurement sites 102) when the object 100 is disposed within the measurement region 512. The metrology controller 516 is configured to designate one or more zones within the measurement region 512 as a measurement site where the depth-wise composition of the object 100 is to be determined. The metrology controller 516 can further be configured to control the measurement system 514 to determine the depth-wise composition of the object 100 at the designated measurement sites.

In one embodiment, the metrology tool 510 includes a chamber having an interior which defines the measurement region 512. The chamber may be provided as any suitable type in another embodiment, the metrology tool 510 includes a gas-curtain generator configured to produce a flow of inert gas (e.g., air, nitrogen, argon, etc.) define a perimeter of the measurement region 512. A pressure within the measurement region 512 may be maintained in a range from 0.1 atm to 5 atm. It, will be appreciated, however, that the pressure within the measurement region 512 may be less than 0.1 atm or greater than 5 atm. Moreover, the atmosphere within the measurement region may be at least substantially inert. Although the measurement region 512 is illustrated as being outside of each of the first process apparatus 502 and the second process apparatus 504, it will be appreciated that the metrology tool 510 may be configured such that the measurement region 512 is disposed within the first process apparatus 502 or the second process apparatus 504. For example, the measurement region 512 may be defined within a process chamber of the first or second process apparatus 502 or 504.

The measurement system 514 may be provided as suitable system capable of determining the depth-wise composition of the object 100 as discussed above. For example, the measurement system 516 may be provided as a photoluminescence system, a spectroscopic ellipsometry system, a confocal microscopy system, a GDOES system, a GDMS system, a LAICPMS system, a LAICPOES system, a LIBS system, a SIMS system, a FIBOES system, or the like or a combination thereof. The measurement system 514 may communicate the determined depth-wise object composition to the metrology controller 516 as composition data. In one embodiment, the measurement system 514 is an LAICPMS or LASICPOES system and the measurement region 512 is defined by a chamber such as a non-contact ablation chamber, a chamber as exemplarily described in co-pending U.S. patent application Ser. No. 13/336,991, filed Dec. 23, 2011 (which is incorporated herein by reference in its entirety).

Figure 6:
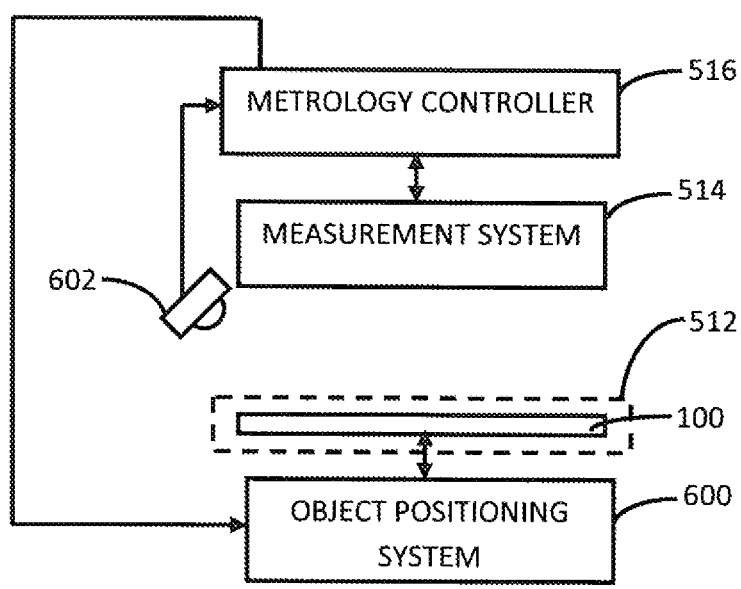
FIG. 6 is schematic view illustrating one embodiment of the metrology tool shown in FIG. 5.

Referring to FIG. 6, the metrology tool 510 may optionally include an object positioning system 600 configured to align the object 100 relative to the measurement system 514. The object positioning system 600 may be provided as a stage configured to move the object 100 (e.g., in X-, Y- and/or Z-directions, R-, Θ and/or Z-directions, or the like or a combination thereof) relative to the measurement system 514. In another embodiment, at least a portion of the measurement system 514 may be configured to move relative to the object 100. Movement of one or both of the object positioning system 600 and the measurement system 514 may be accomplished manually or by way of one or more motors, actuators, etc., operating under control of, for example, the metrology controller 516.

Movement of one or both of the object positioning system 600 and the measurement system 514 may be performed to align the object 100 with the measurement system 514 in a known or desired manner. In one embodiment, the metrology tool 510 may further include a device (e.g., a camera 602) to detect the position of the object 100 within the measurement region 512. For example, the camera 602 may detect the position of the object 100 by visually detecting one or more features such as an edge of the object 100 or an alignment mark, device, scribe line, etc., on the object 100. The detected position of the object 100 may be used by the metrology controller 516 to control the movement of measurement system 514 and/or the object 100 (e.g., via the object positioning system 600).

In another embodiment, virtual alignment of the object 100 relative to the measurement system 514 may be accomplished within the metrology controller 516 by adjusting a spatial position of the designated measurement sites within the measurement region 512. In such an embodiment, alignment of the designated measurement sites relative to the object 100 within the measurement region 512 may be accomplished by aligning the designated measurement sites relative to one or more features detected by the camera 602.

Figure 5:
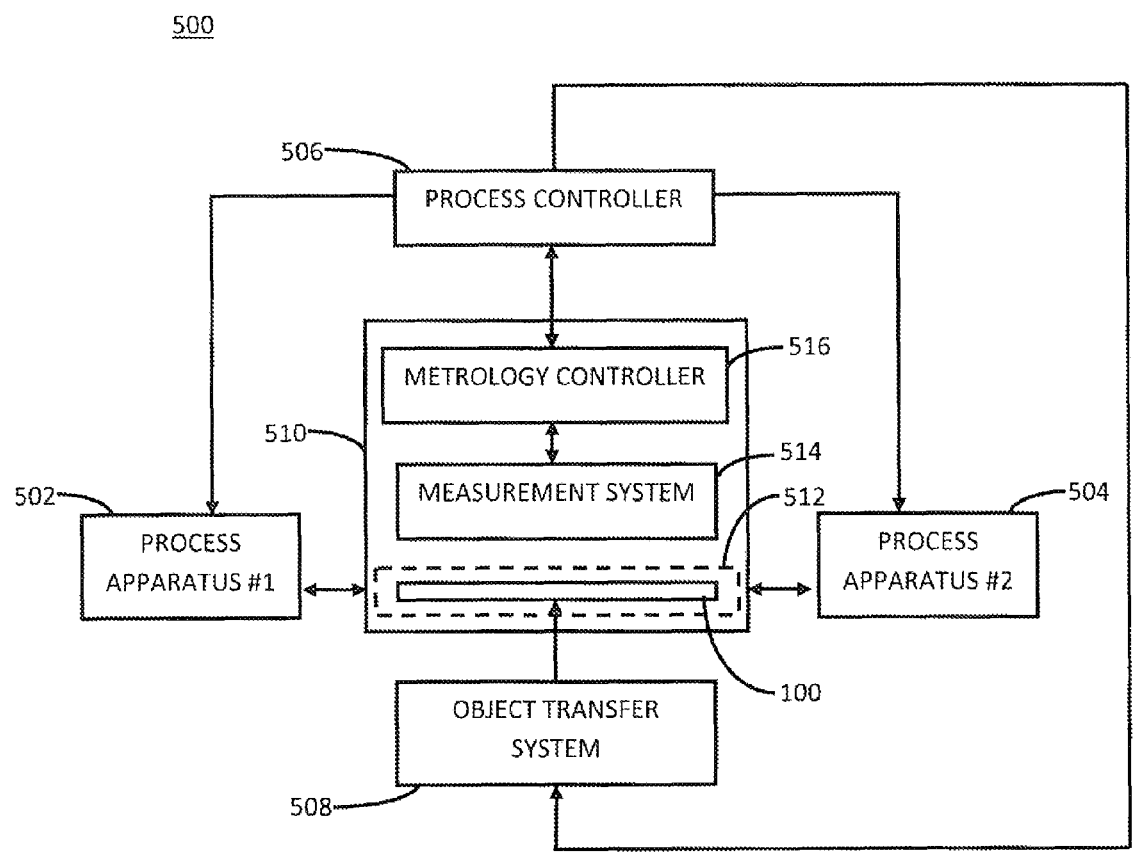
FIG. 5 is schematic view illustrating a metrology tool provided within a manufacturing system according to one embodiment.

Referring to FIGS. 5 and 6, the metrology controller 516 can be configured to quantitatively estimate one or more regional properties of the object 100 based upon the composition data received from the measurement system 514. In one embodiment, the metrology controller 516 may communicate the one or more quantitatively estimated regional properties of the object 100 to the process controller 506, to an output device (e.g., a monitor, a printer, etc.), or the like or a combination thereof, as regional property data. In another embodiment, the metrology controller 516 may communicate the composition data to the process-controller 506. In turn, the process controller 506 may modify an operation of one or more components of the manufacturing system 500 based on the received composition data, regional property data or a combination thereof.

For example, if the data communicated by the metrology controller 516 indicates that the first process apparatus 502 did not fabricate some aspect of the object 100 (e.g., the MQW LED structure) as desired, the process controller 506 may modify an operation of the first process apparatus 502 to ensure that the first process apparatus 502 fabricates MQW LED structures as desired. In another example, if the data communicated by the metrology controller 516 indicates that the first process apparatus 502 did not fabricate some aspect of the object 100 (e.g., the MQW LED structure) as desired, the process controller 506 may modify an operation of the second process apparatus 504 to compensate for the manner in which the first process apparatus 502 fabricated by the first process apparatus 502. Thus, a manufacturing process carried out by the manufacturing system 500 can be monitored, in real-time, using data generated by the metrology tool 510. In yet another example, the process controller 506 may control an operation of the object transfer system 508 to route the object 100 to another process apparatus (not shown) or location within the manufacturing system 500 to optimize the manner in which the as-fabricated object 100 based on data communicated by the metrology controller 516.

Figure 2:
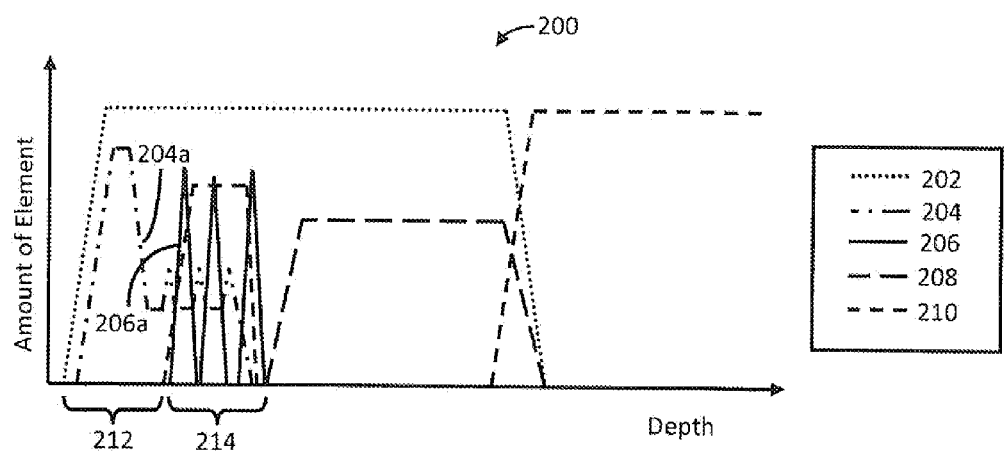
FIG. 2 is chart schematically illustrating a depth-wise object composition of the object taken at an arbitrary measurement site shown in FIG. 1.
Figure 7:
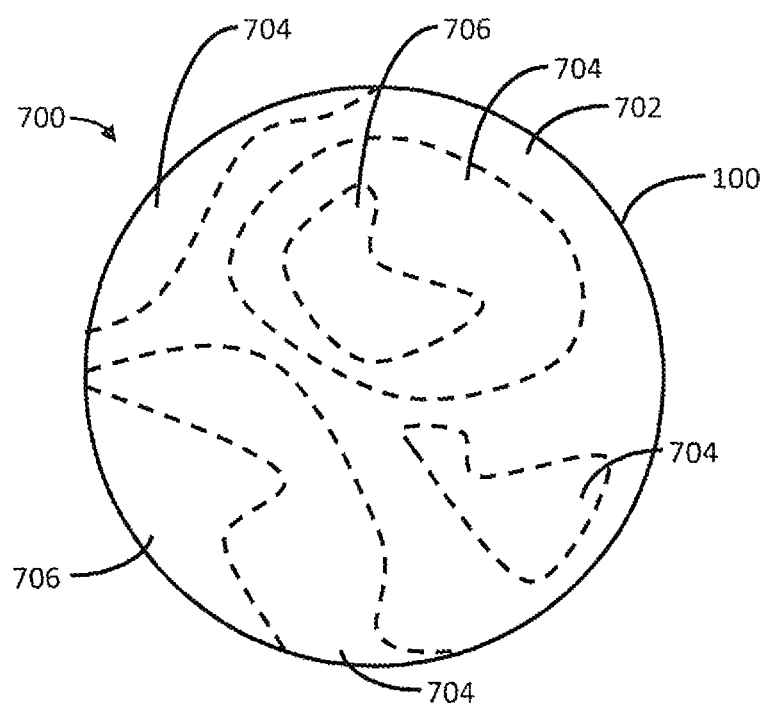
FIG. 7 is a plot schematically illustrating an estimated quantitative variation of a regional property of an object, spatially distributed across the object.

In one embodiment, the metrology controller 516 may communicate the composition data and the regional property data to a user-accessible output device such as a computer monitor, a printer, or the like or a combination thereof. When communicated to such a user-accessible output device, the compositional data may be represented in a visual format as shown in FIG. 2. When communicated to such a user-accessible output device, the regional property data may be meaningfully represented to a user. For example, and continuing with the example embodiment discussed above with respect to FIG. 2, regional property data may be visually represented as a two-dimensional plot illustrating the variation of a regional property (e.g., forward voltage of the MQW LED structure) as a function of spatial location across the object 100). As exemplarily illustrated in FIG. 7, quantitative estimates of the regional property failing into different ranges may be represented as visually distinct regions 702, 704 and 706. Although data for only one regional property is visually represented in FIG. 7 as a two-dimensional plot, it will be appreciated that regional property data may be visually represented in any other form (e.g., as a three-dimensional plot illustrating the variation of a regional property as a function of spatial location across and within the object). It will also be appreciated that data for multiple regional properties may be visually represented simultaneously.

Referring back to FIGS. 5 and 6, the metrology controller 516 can generally include operating logic (not shown) that defines various control, management and/or regulation functions, and may be in the form of dedicated hardware, such as a hardwired state machine, a processor executing programming instructions, and/or a different form as would occur to those skilled in the art. Operating logic may include digital circuitry, analog circuitry, or a hybrid combination of both of these types. In one embodiment, the operating logic includes a programmable microcontroller or microprocessor, that can include one or more processing units arranged to execute software and/or firmware stored in memory (not shown). Memory can include one or more types including semiconductor, magnetic, and/or optical varieties, and/or may be of a volatile and/or nonvolatile variety. In one embodiment, memory stores programming instructions of operating logic. Alternatively or additionally, memory may store data that is manipulated by operating logic. In one arrangement, operating logic and memory are included in a controller/processor form of operating logic that manages and controls operational aspects of the measurement system 514, as well as other components of the metrology tool 510 (e.g., object positioning system 600, device 602, etc.) although in other arrangements they may be separate.

The following embodiments are described in sufficient detail to enable those skilled in the art to make and use the invention. It is to be understood that other embodiments would be evident based on the present disclosure, and that process or mechanical changes may be made without departing from the scope of the present invention defined in the claims. In the following description, numerous specific details are given to provide a thorough understanding of the invention. However, it will be apparent that the invention may be practiced without these specific details. In order to avoid obscuring the present invention, some well-known system configurations and process steps are not disclosed in detail. Likewise, the drawings showing embodiments of the system are schematic and not to scale and, particularly, some of the dimensions are for the clarity of presentation and are shown greatly exaggerated in the drawing FIGS. In addition, where multiple embodiments are disclosed and described having some features in common, for clarity and ease of illustration, description, and comprehension thereof, similar and like features one to another will ordinarily be described with like reference numerals.

What is claimed is:

1. A method comprising:
   determining, at a measurement site within an object, a composition of the object as a function of depth within the object; and
   based on the determining, quantitatively estimating at least one property of the object within a region of the object adjacent to the measurement site.

2. The method of claim 1, further comprising determining the composition of the object as a function of depth within the object at a plurality of discrete measurement sites within the object.

3. The method of claim 2, further comprising, based on the determining, determining quantitatively estimating at least one property of the object within a region of the object adjacent to the plurality of measurement sites.

4. The method of claim 1, wherein the object includes a substrate.

5. The method of claim 4, wherein the object includes at least one layer disposed on the substrate.

6. The method of claim 5, wherein the at least one layer is an epitaxial layer.

7. The method of claim 1, wherein, at the measurement site, determining the composition of the object as a function of depth within the object comprises:
   obtaining a sample of the object; and
   analyzing the composition of the sample.

8. The method of claim 7, wherein, at the measurement site, determining the composition of the object as a function of depth within the object further comprises:
   obtaining a plurality of discrete samples from different depths within the object; and
   analyzing the composition of at least two of the plurality of discrete samples.

9. The method of claim 7, wherein obtaining the sample of the object comprises directing a pulse of laser energy onto the object.

10. The method of claim 7, wherein obtaining a sample of the object includes removing the portion of the object while exposing a pressure in a range from 0.1 atm to 5 atm.

11. The method of claim 7, wherein analyzing the composition of the sample of the object includes analyzing the composition by mass spectroscopy (MS).

12. The method of claim 7, further comprising determining a depth within the object from which at least a portion of the sample was obtained.

13. The method of claim 1, wherein quantitatively estimating the at least one property includes quantitatively estimating at least one property selected from a group consisting of a composition of the object, an electrical property of the object, an optical property of the object, a thermal property of the object, a mechanical property of the object and a magnetic property of the object.

14. A method of monitoring a manufacturing process implementable by manufacturing system including at least one process apparatus, the method comprising:
   determining, at a measurement site within an object, a composition of the object as a function of depth within the object;
   based on the determining, quantitatively estimating at least one property of the object within a region of the object adjacent to the measurement site;
   generating regional property data based on the quantitative estimating; and
   providing the estimated property data to a controller coupled to a process apparatus of the manufacturing system configured to manufacture the object or modify the object.

15. The method of claim 14, wherein the object has a maximum dimension of at least 50 mm.

16. The method of claim 14, wherein the object has a maximum dimension of at least 150 mm.

17. The method of claim 14, wherein the determining is performed outside a process apparatus of the manufacturing system.

18. The method of claim 17, further comprising, before determining the composition of the object, receiving the object from a first process apparatus of the manufacturing system, wherein the first process apparatus is configured to manufacture the object.

19. The method of claim 18, further comprising, after determining the composition of the object, transferring the object to a second process apparatus of the manufacturing system, wherein the second process apparatus is configured to modify the object.

20. The method of claim 14, wherein providing the estimated property data comprises providing the estimated property data to a controller coupled to a process apparatus of the manufacturing system configured to manufacture the object, wherein the process apparatus is a metal organic chemical vapor deposition apparatus.

21. A method comprising:
   providing a metrology tool including:
      a measurement region within which an object is at least partially disposable;
      a controller configured to designate a zone within the measurement region as a measurement site; and
      a measurement system coupled to the controller, wherein the measurement system is configured to perform a compositional analysis of material occupying the measurement site;
   disposing at least a portion of an object within the measurement region, wherein the object includes a feature;
   aligning the feature and a location of the measurement site within the measurement region relative to each other; and
   performing a compositional analysis of the portion of the disposed object occupying the measurement site, including determining a composition of the portion of the disposed object at the occupied measurement site as a function of depth within the object.

22. The method of claim 21, wherein the controller is configured to designate a plurality of discrete measurement sites within measurement region, wherein the method further comprises:
   aligning the feature with respect to the measurement system such that a portion of the disposed object occupies a measurement site; and
   performing a compositional analysis of a portion of the disposed object at the occupied measurement site.

23. The method of claim 21, further comprising quantitatively estimating at least one property of a portion of the object based on the determining.

24. The method of claim 21, wherein aligning the feature and a location of the measurement site relative to each other includes at least one selected from the group consisting of:

adjusting a position of the object, adjusting a position of the measurement system, and adjusting a spatial position of the measurement site within the measurement region.

* * * * *